(12) United States Patent
Horan (10) Patent No.: US 6,921,263 B1
(45) Date of Patent: Jul. 26, 2005

(54) ADJUSTABLE DENTAL INSTRUMENT HAVING A MULTI-DETENT LATCH

(76) Inventor: Terrence L. Horan, 75 Vermont Rte. 15, Jericho, VT (US) 05465

(*) Notice: Subject to any disclaimer, the term of this patent is extended or adjusted under 35 U.S.C. 154(b) by 230 days.

(21) Appl. No.: 10/165,061

(22) Filed: Jun. 7, 2002

Related U.S. Application Data (60) Provisional application No. 60/296,571, filed on Jun. 8, 2001.

(51) Int. Cl.[7] ............................................. A61C 3/00
(52) U.S. Cl. ...................... 433/157; 606/208; 81/318; 81/325
(58) Field of Search ............................. 433/157, 159, 433/163; 606/208; 81/318, 319, 323, 325

(56) References Cited

U.S. PATENT DOCUMENTS

| | | |
|---|---|---|
| 290,103 A | 12/1883 | Paul |
| 636,285 A | 11/1899 | Pinson |
| 649,234 A | 5/1900 | Chiavard |
| 673,541 A | 5/1901 | Hussey |
| 770,162 A | 9/1904 | Chase |
| 778,977 A | 1/1905 | Johnson |
| 1,202,698 A | 10/1916 | Ford |
| 1,412,130 A | 4/1922 | Onderdonk |
| 1,470,313 A * | 10/1923 | Woolen .......................... 29/224 |
| 2,439,785 A * | 4/1948 | Feitl et al. ....................... 29/229 |
| 2,670,015 A * | 2/1954 | Reynolds ....................... 140/121 |
| 2,776,152 A | 1/1957 | Ianuzzi ........................... 287/12 |
| 2,962,024 A * | 11/1960 | Raymond ........................ 606/208 |
| 3,368,553 A | 2/1968 | Kirby ............................. 128/62 |
| 3,470,872 A * | 10/1969 | Grieshaber .................... 600/217 |
| 3,748,741 A | 7/1973 | Yerkes, Jr. ....................... 32/71 |
| 3,898,738 A | 8/1975 | Linder ............................. 32/41 |
| 4,364,730 A | 12/1982 | Axelsson ....................... 433/141 |
| 4,620,813 A | 11/1986 | Lacher ............................. 403/93 |

(Continued)

OTHER PUBLICATIONS

Product Information Sheet entitled Detsch® Scalpel Handles-Blade Breaker-Scalpel Blades; G. Hartzell & Son, date: at least as early as Jan. 19, 1998.

(Continued)

*Primary Examiner*—Ralph A. Lewis
(74) *Attorney, Agent, or Firm*—Downs Rachlin Martin PLLC (57) ABSTRACT

A dental instrument (10) having a tool (12) with a tip (56) capable of being rapidly adjusted and fixed in a variety of orientations relative to an instrument body (14). The instrument comprises opposing jaws (16, 22) having concave surfaces (18, 24). One jaw (16) is attached to one end of the instrument body, while the other jaw (22) is attached to the end of a lever arm (20). The lever arm is pivotally attached to the instrument body and is pivotal between a first (closed) position (P1), a second (intermediate) position (P2) and a third (open) position (P3). The lever arm includes a latch (26) having first and second catches (34, 36) that each releasably engage a rim (42) of an aperture (40) in the instrument body so as to retain the lever arm in the first (closed) position and the second (intermediate) position, respectively. The tool includes a spherical jaw-engaging end (54) sized to be tightly engaged by the concave surfaces of the jaws when the lever arm is in the first (closed) position, thereby preventing the tool from moving relative to the instrument body.

23 Claims, 7 Drawing Sheets

U.S. PATENT DOCUMENTS

| | | | |
|---|---|---|---|
| 4,759,713 A | 7/1988 | Heiss et al. | 433/141 |
| 4,976,617 A | 12/1990 | Carchidi | 433/141 |
| 4,997,382 A | 3/1991 | Berger | 433/163 |
| 5,464,413 A * | 11/1995 | Siska et al. | 606/151 |
| 5,851,211 A | 12/1998 | Khoury | 606/147 |
| 5,928,263 A | 7/1999 | Hoogeboom | 606/205 |
| 6,159,217 A * | 12/2000 | Robie et al. | 606/88 |
| 6,193,514 B1 | 2/2001 | Horan | 433/141 |

OTHER PUBLICATIONS

Clinician's Choice Dental Products Inc. (p. 21 from catalog) (no date).

* cited by examiner

ADJUSTABLE DENTAL INSTRUMENT HAVING A MULTI-DETENT LATCH

CROSS-REFERENCE TO RELATED APPLICATION

This application claims the benefit of priority of U.S. Provisional Patent Application No. 60/296,571, filed Jun. 8, 2001 and entitled "Adjustable Dental Instrument."

FIELD OF THE INVENTION

The present invention relates to the field of mechanical instruments. More particularly, the present invention is directed to an adjustable dental instrument having a multi-detent latch that can hold a tool tightly in a variety of positions and allows the tool to be quickly and easily moved from one orientation to another and removed from the instrument.

BACKGROUND OF THE INVENTION

In the practice of dentistry, it is often necessary for a dentist to perform dental procedures at various orientations relative to the dental work. This typically requires the dentist to have a variety of dental instruments at his/her disposal, each having at one or both ends a fixed tool with a tip having a given shape and orientation. Alternatively, the dentist can use a dental instrument comprising an instrument body that accepts a tool having a tip. The tool can be adjusted so the tip can take on a variety of orientations, i.e., positions relative to the instrument body. In addition, with some instruments, the tool may be replaced with another tool having a different tip configuration. For such an adjustable dental instrument, it is important that the tool be capable of being rapidly adjusted to a particular orientation and then fixed tightly in place within the instrument body. It is also important that the instrument body and tool be amenable to being rapidly cleaned for subsequent re-use.

Various conventional instruments are available that utilize removable and/or adjustable tools. However, these instruments have various shortcomings, including: relatively cumbersome adjustability; limited positionability of the tool tip; uncertainty in the strength of the grip on the tool; complexity of the clamping mechanism; and relatively weak grip on the tool. The present invention overcomes these and other shortcomings of conventional dental instruments.

SUMMARY OF THE INVENTION

One aspect of the invention is an instrument comprising a body and a lever arm pivotably attached to the body so as to have a first pivoted position relative to the body and a second pivoted position relative to the body that is different from the first pivoted position. The instrument also includes a rim attached to either the body or the lever arm. The rim defines at least a portion of an aperture. In addition, the instrument includes a latch having a first end and a second end spaced from the first end. If the rim is attached to the body, then the first end of the latch is attached to the lever arm, and if the rim is attached to the lever arm, then the first end of the latch is attached to the body. The latch also includes a first catch, located proximate the second end, for holding the lever arm in the first pivoted position when the first catch is engaged with the rim. In addition, the latch includes a second catch, located proximate the second end, for holding the lever arm in the second pivoted position when the second catch is engaged with the rim. The second end of the latch is movable relative to the first end for allowing a user to disengage each of the first and second catches from the rim when desired. Finally, the instrument includes first and second jaws, wherein at least one of the first and second jaws is operatively coupled with the lever arm so that the at least one of the first and second jaws moves in conjunction with the lever arm when a user pivots the lever arm from the first pivoted position to the second pivoted position.

Another aspect of the present invention is a method of opening jaws of an instrument comprising a lever arm, a first stop, a latch that includes a first catch and a second catch spaced from the first catch, and a movable end having a finger-engaging surface for moving the lever arm from a first position to a second position. A first step in the method involves engaging a finger with the finger-engaging surface. Then, the first catch is disengaged from the rim by moving the movable end of the latch in a first direction with said finger. Next, the lever arm is pivoted a first amount to open the jaws a corresponding amount. Finally, the second catch is engaged with the rim.

BRIEF DESCRIPTION OF THE DRAWINGS

For the purpose of illustrating the invention, the drawings show a form of the invention that is presently preferred. However, it should be understood that the present invention is not limited to the precise arrangements and instrumentalities shown in the drawings, wherein.

DETAILED DESCRIPTION OF THE DRAWINGS

Figure 1A:
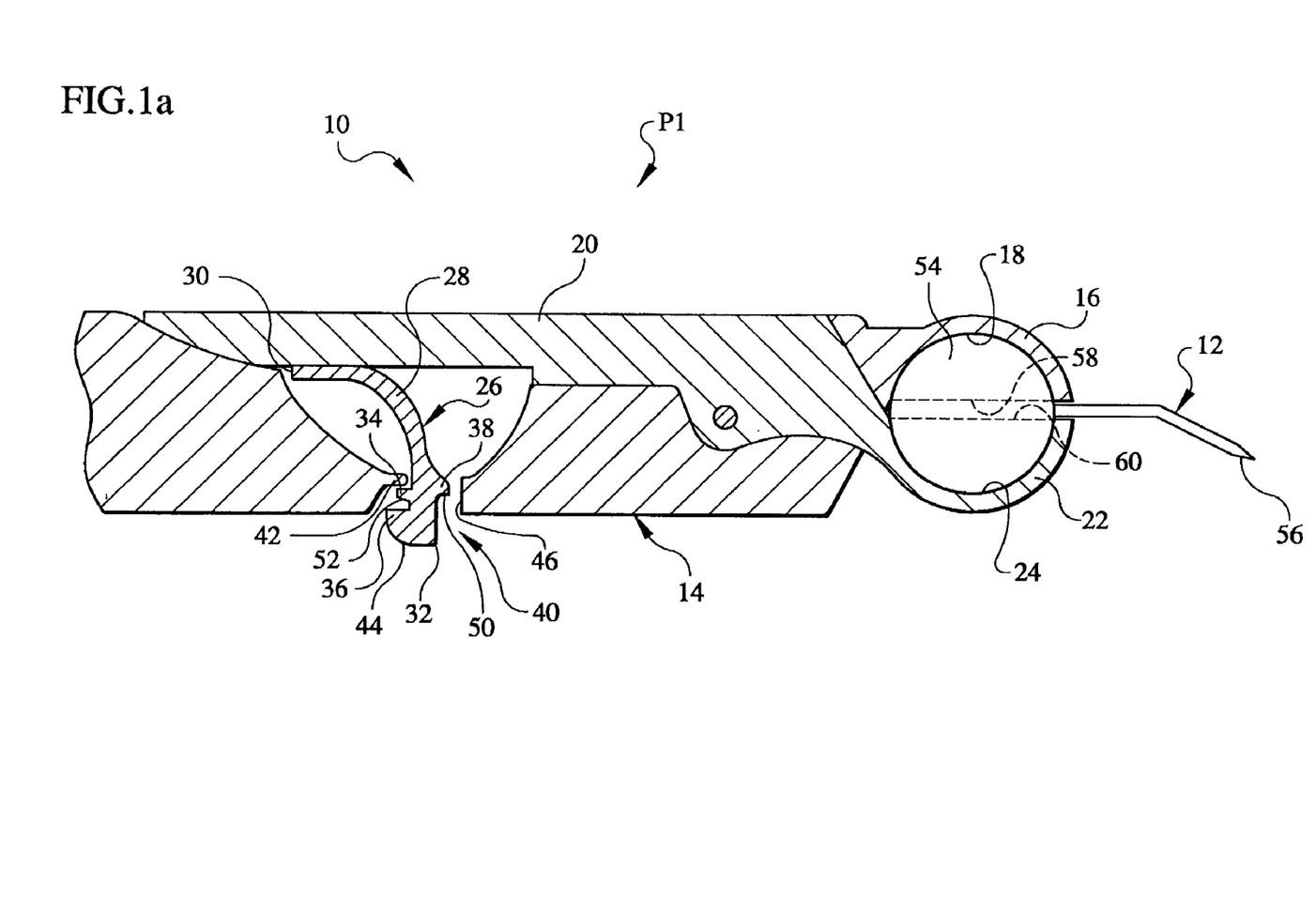
FIGS. 1a–1c are enlarged partial cross-sectional views along the longitudinal axis of a dental instrument of the present invention having a double-catch latch showing the lever arm in, respectively, a closed position, an intermediate position, and an open position.
Figure 1B:
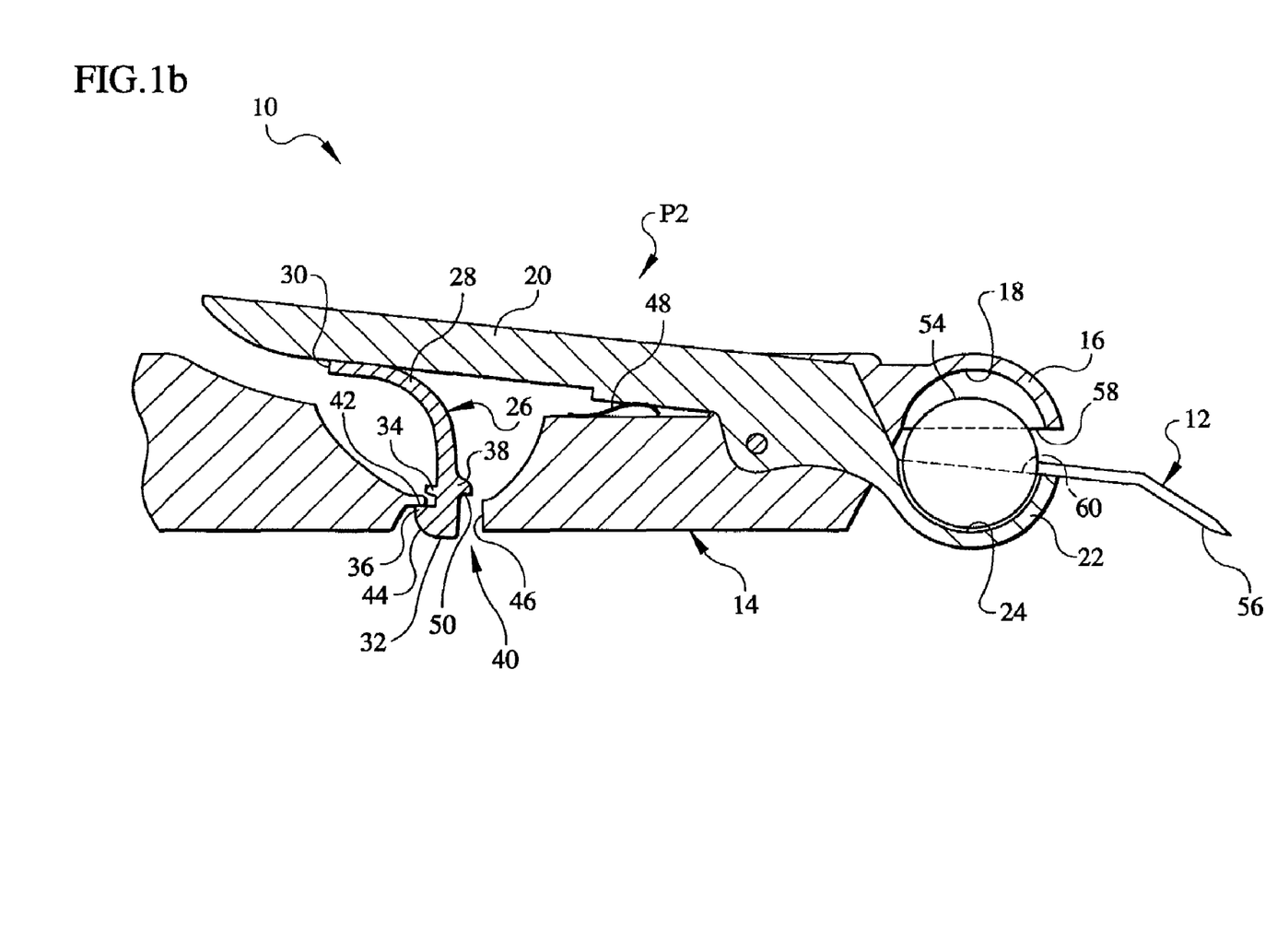
Figure 1C:
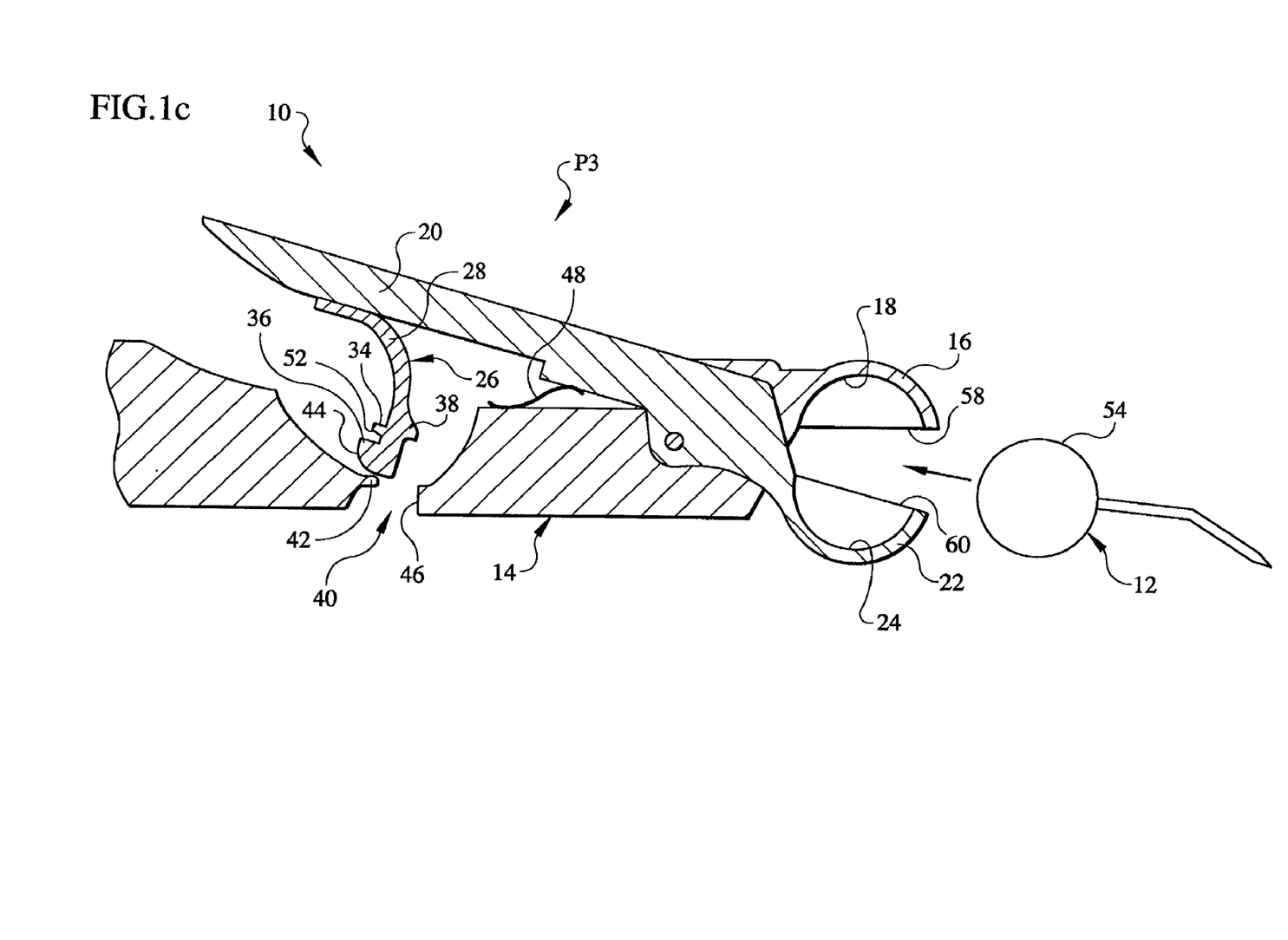

Referring now to the drawings, wherein like numerals indicate like elements, FIGS. 1a–1c show in accordance with the present invention an adjustable dental instrument, which is generally denoted by the numeral 10. Instrument 10 allows a user to adjust the instrument to several positions that permit the user to install a tool 12, adjust the tool to a desired orientation, and firmly grasp the tool by operating an inventive latch means that provides such adjustability. It is noted that instrument 10 is generally similar in a number of respects to the like instrument disclosed in U.S. Pat. No. 6,193,514 to Horan, the inventor of the present invention. U.S. Pat. No. 6,193,514 is incorporated by reference herein in its entirety. As discussed below, instrument 10 of the present invention may include any one or more of the various features, and generally includes much of the same functionality, of the instrument disclosed in U.S. Pat. No. 6,193,514.

Instrument 10 may comprise an instrument body 14 that includes a first jaw 16 having an inner concave surface 18. Instrument 10 may further comprise a lever arm 20 that includes a second jaw 22 having an inner concave surface 24 and that is pivotally attached to instrument body 14 at a pivot point P, which may be located proximate the jaw end of the instrument body. Jaws 16, 22 may extend generally along the longitudinal central axis of instrument 10 similar to that shown in U.S. Pat. No. 6,193,514. However, those skilled in the art will appreciate that jaws 16, 22 may alternatively be curved, e.g., in a manner akin to a curved hemostat, or otherwise curved and/or shaped in a manner other than that shown in the drawings.

Instrument 10 may have a generally circular cross-sectional shape in a direction transverse to its longitudinal central axis. In this connection, instrument body 14 and lever arm 20 may be shaped so as to form the circular shape when the lever arm is in the closed position shown in FIG. 1, i.e., the instrument body may have a recessed region for receiving therein a like-shaped lever arm. Of course, instrument 10 may have any transverse cross-sectional shape desired and lever arm 20 may engage instrument body 14 in any suitable manner. For example, in an alternative embodiment, instrument body 14 may be provided with a longitudinal slot for receiving a like-shaped lever arm 20 when jaws 16, 22 are closed (see below) or, alternatively, the instrument body may not include a slot or other recess for receiving a like-shaped lever arm so that the lever arm extends radially away from the instrument body when the jaws are closed.

It is noted that although jaws 16, 22 are shown as being fixedly attached to instrument body 14 and lever arm 20, respectively, the jaws may be otherwise operatively coupled with the lever arm and/or instrument body such that one or both jaws move relative to the instrument body when a user moves the lever arm relative to the instrument body. For example, jaws 16, 22 may be located generally remote from instrument body 14 and lever arm 20, such as in the manner shown in U.S. Pat. No. 5,928,263 to Hoogeboom, which is incorporated herein by reference. In the Hoogeboom patent, one of the jaws is shown as being pivotable and coupled to a lever arm by a linkage rod that moves that jaw in conjunction with the lever arm when a user pivots the lever arm. Alternatively, both jaws may be pivotable and similarly coupled to the lever arm by one or more linkage rods, or other linkage mechanism. Those skilled in the art will readily appreciate the changed required to implement alternative jaw couplings, such as those just mentioned.

Lever arm 20 may be pivotable between a closed position P1 (FIG. 1a), an intermediate position P2 (FIG. 1b), and an open position P3 (FIG. 1c). Generally, in closed position P1, instrument 10 may firmly grip tool within jaws 16, 22. In intermediate position P2, jaws 16, 22 may have either a loose grip on tool or otherwise contain the tool so that it cannot fall out of the jaws. An advantage of having an open position P3 is that the process of cleaning the parts of the instrument within instrument body 14 may be simplified. Positions P1–P3 are described in more detail in U.S. Pat. No. 6,193,514.

In an exemplary embodiment, lever arm 20 is approximately 60 mm long, and pivot point P is located approximately 18 mm from the tip of second jaw 22. Also, the total length of lever arm 20 and second jaw 22 is approximately 80 mm. This configuration provides a mechanical advantage of approximately 3 to 1, which is suitable for providing a sufficient clasping force, as described below. The present invention encompasses lever arms 20 of varying length and/or configurations, with the length of the lever arm being selected to achieve the desired clamping force and configurations being selected for a number of reasons, including ergonomics and the intended use of instrument 10, among others.

With continuing reference to FIGS. 1a–1c, instrument 10 may further comprise a latch 26 attached lever arm 20 that, in cooperation with various structures on instrument body 14, provides instrument 10 with multiple detents for holding the lever arm relatively securely in each of closed position P1 and intermediate position P2. Latch 26 may include a curvilinear, elongate member 28 having a fixed first end 30 and a movable second end 32. Latch 26 may be secured to lever arm 20 in a conventional manner at and/or adjacent first end 30 and may include a first catch 34, a second catch 36, and an opening guide 38, all located generally proximate second end 32. Latch 26 may be made from a resilient material that allows it to be elastically deformed so that second end 32 may be moved relative to first end 30 to provide the latching functions described below. Those skilled in the art will appreciate that second end 32 of latch 26 may be made movable using means other that the elongate flexible latch shown. For example, first end 30 of latch may be pivotably attached to lever arm 20 and biased into engagement (see below) with instrument body 14 by, e.g., a spring, such as a cantilever spring, a rotational spring, or a coil spring, among others, or a resilient body, such as a rubber bumper.

Latch 26 may be attached to lever arm 20 as shown or, alternatively, may be attached to instrument body 14. Those skilled in the art will readily understand how this change in location of latch 26 may be implemented by generally switching the corresponding inter engaging parts, described below, between lever arm 20 and instrument body 14. In addition, although latch 26 is shown as being actuatable, i.e., movable, in fore and aft directions with respect to instrument 10, those skilled in the art will appreciate that the latch may be actuatable in other directions as well, such as side to side.

Corresponding to latch 26, instrument body 14 may include an aperture 40 defined by a rim 42 that defines a stop for alternately engaging first and second catches 34, 36 to hold lever arm 20, respectively, in closed position P1 and intermediate position P2. A user may disengage each of first and second catches 34, 36 from rim 42 by moving second end 32 of latch 26 forward, i.e., in a direction generally toward jaws 16, 22. When first and second catches 34, 36 are located on opposite sides of rim 42 as shown in FIG. 1b, lever arm 20 is in intermediate position P2.

When first catch 34 is positioned below rim 42 as shown in FIG. 1a, lever arm 20 is in closed position P1. To move lever arm 20 between closed position P1 and intermediate position P2, e.g., to adjust tool 12 such as one of tools 12 shown in FIGS. 2a–2c, held within jaws 16, 22, a user may move second end 32 of latch 26 in a direction generally toward the jaws, i.e., forward, using a finger engaged with surface 44, which may be curved as shown. As the user continues to move second end 32 forward, guide 38 eventually contacts an anterior portion 46 of rim 42, preventing further forward movement of latch 26, and allowing second catch 36 to engage rim 42. At this point, lever arm 20 may be rotated clockwise as a result of a biasing spring 48 that biases the lever arm in a direction toward open position P3 (FIG. 1c). Biasing spring 48 may be any type of spring, such as the cantilever spring shown, a coil spring, a leaf spring, rotational spring, or any resilient body that provides a suitable biasing force. Of course, in an alternative embodiment, biasing spring may be omitted so that user may have to open lever arm 20 manually. As lever arm 20 rotates clockwise, second catch 36 may engage rim 42 to secure the lever arm into its intermediate position P2.

When lever arm 20 is in intermediate position P2, a user may move the lever arm to open position P3, e.g., to remove a tool from jaws 16, 22 and/or to clean instrument 10, by moving second end 32 of latch 26 forward in a manner similar to the manner described above in connection with moving the lever arm from closed position P1 to intermediate position P2. At this point, a notch 50 may allow guide 38 to clear anterior portion 46 of rim 42 so that second catch 36 may move past rim 42. From intermediate position P2, the user may also move lever arm 20 to closed position P1 simply by moving the lever arm toward instrument body 14 so that a beveled surface 52 of first catch 34 slidably engages rim 42 of the instrument body. Similarly, to move lever arm 20 to intermediate position P2 from open position P3, the user need simply move the lever arm toward instrument body 14 so that surface 44 slidably engages rim 42.

It is noted that the change in position of lever arm 20 between intermediate position P2 and closed position P1 with respect to instrument body 14, i.e., the rotation of the lever arm about pivot point P may be relatively small in some embodiments of the present invention. This is so, because in some embodiments, intermediate position P2 may be such that concave surfaces 18, 24 of jaws 16, 22 contact an jaw-engaging end 54 of tool 12, albeit relatively loosely, and in closed position P1 the concave surfaces continue to contact the jaw-engaging end, but more firmly. Thus, if jaw-engaging end 54 of tool 12 is made of a largely incompressible material, such as metal, the only change in position of lever arm 20 between intermediate and closed positions P2, P1 may be due to substantially only bending of the lever arm. In other embodiments, however, the change in position of lever arm 20 may be relatively large if the location of second catch 32 permits jaws 16, 22 to be opened so that jaw-engaging end 54 of tool 12 can be moved about within the jaws when the lever arm is in intermediate position P2 (but without the jaw-engaging end to pass through the space between the jaws).

Figure 2A:
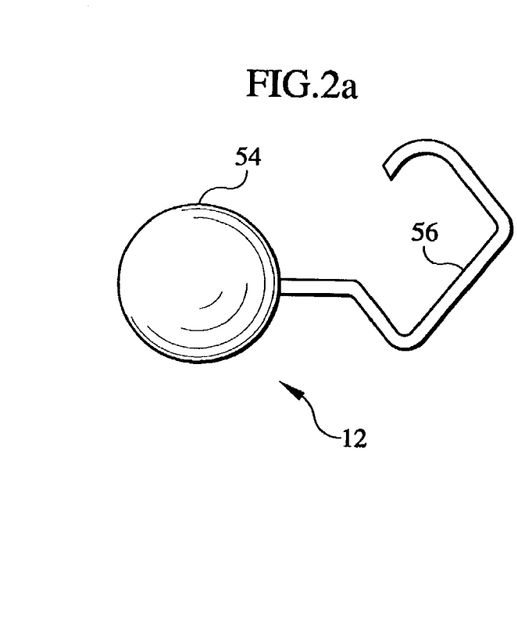
FIGS. 2a–2c show three different types of tools suitable for use with the dental instrument of the present invention.
Figure 2B:
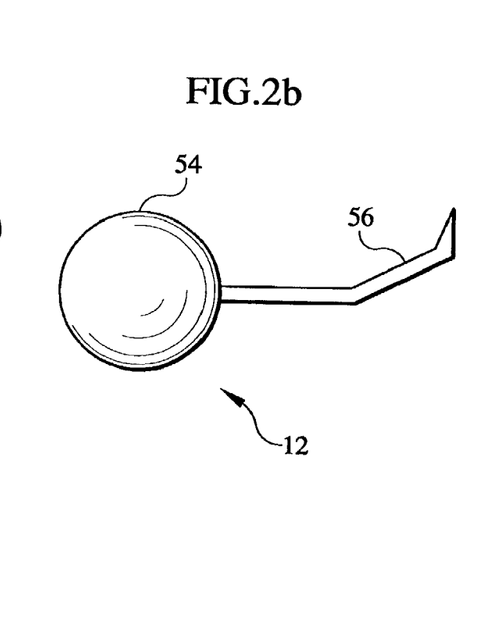
Figure 2C:
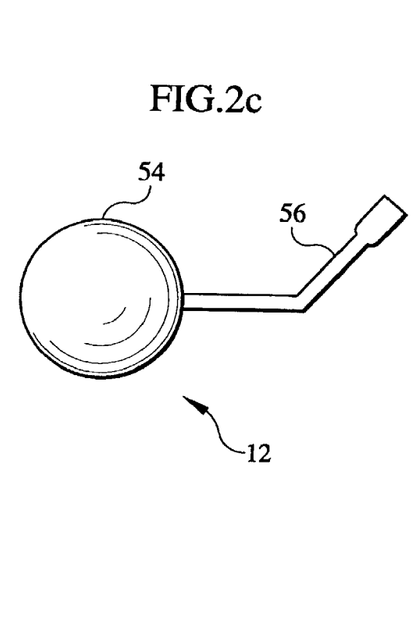

With continuing reference to FIG. 1 and also referring to FIGS. 2a–2c, instrument 10 may be used to engage tool 12 having a spherical jaw-engaging end 54 that may be sized to be tightly engaged by jaw concave surfaces 18, 24 of jaws 16, 22, respectively, when lever arm 20 is in first position P1. In an exemplary embodiment of the present invention, concave surfaces 18, 24 may each have a radius of curvature of 6 mm to 8 mm (e.g, 7 mm) and jaw-engaging end 54 has a matching radius, or one that is slightly larger. Jaw-engaging end 54 may comprise an incompressible material, such as stainless steel, or a compressible material, such as rubber or silicone. Tool 12 may also include a tool tip 56, which can have any one of a number of configurations common in dental instruments, such as shown in FIGS. 2a–2c.

An important aspect of the present invention is that jaw-engaging end 54 may be engaged with sufficient force by concave surfaces 18, 24 of jaws 16, 22, respectively, so that the jaw-engaging end 54 remains immobile within the jaws and does not move relative to instrument body 14 when conventional dental-procedure forces are applied to tip 56. This may be accomplished by designing concave surfaces 18, 24 and jaw-engaging end 54 to have either an interference fit or a precision fit when lever arm 20 is in first position P1. The length of lever arm 20 and the location of pivot point P may be selected to provide the leverage necessary to provide jaws 16, 22 with sufficient force to strongly clasp jaw-engaging end 54. In additional, jaws 16, 22 may include a compressible liner on surfaces 18, 24 to facilitate a snug grip with jaw-engaging end 54.

It is noted that although jaw-engaging end 54 of tool 12 is shown as being spherical to conformally engage spherical concave surfaces 18, 24 of jaws 16, 22, the jaw-engaging end and concave surfaces may be another shape, such as cylindrical. In such an embodiment, the central axis of the cylindrical shape of concave surfaces 18, 24 may be perpendicular to the planes defined by outer edges 58, 60 of jaws 16, 22 when instrument 10 is in its closed position P1. Accordingly, when instrument 10 is placed into its intermediate position P2, i.e., the tool-adjustment position, a user may adjust tip 56 of tool 12 about the central axis of the cylindrical jaw-engaging end 54 of the tool to orient the tip into a desired orientation. When the user has moved tip 56 to a desired orientation, the user may lock tool 12 in place by placing instrument 10 into its closed position P1.

In another embodiment, each concave surface 18, 24 may define an elongate groove having, e.g., a rectangular cross-sectional shape. The grooves may be oriented in any direction relative to the central axis of instrument 10, such as parallel or perpendicular to this central axis. Correspondingly, jaw-engaging end 54 of tool 12 may be box shaped and sized so as to be slidable along the grooves defined by concave surfaces 18, 24. When instrument 10 is placed into its intermediate, tool-adjustment position P2, a user may change the position of tool 12 along the grooves. When the user has moved tool 12 to a desired position, the user may lock the tool in place by placing instrument 10 into its closed position P1. It is noted that concave surfaces 18, 24 of jaws 16, 22 and tool 12 may each include teeth (not shown) that mesh with one another when the tool is clamped in instrument 10. Such teeth are shown in U.S. Pat. No. 6,193,514.

Figure 3A:
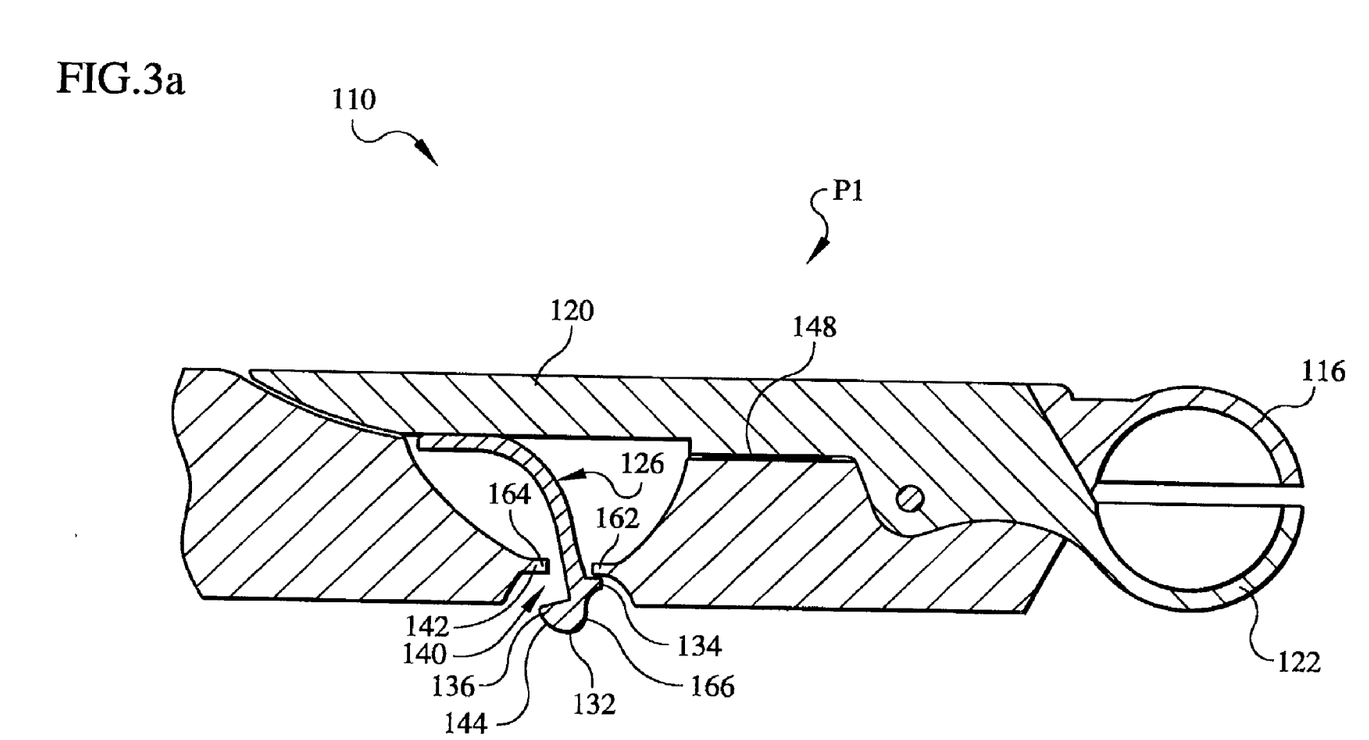
FIGS. 3a and 3b are enlarged partial cross-sectional views along the longitudinal axis of alternative dental instrument of the present invention having a bidirectional double-catch latch in place of the lever showing the lever arm in, respectively, a closed position and an intermediate position.
Figure 3B:
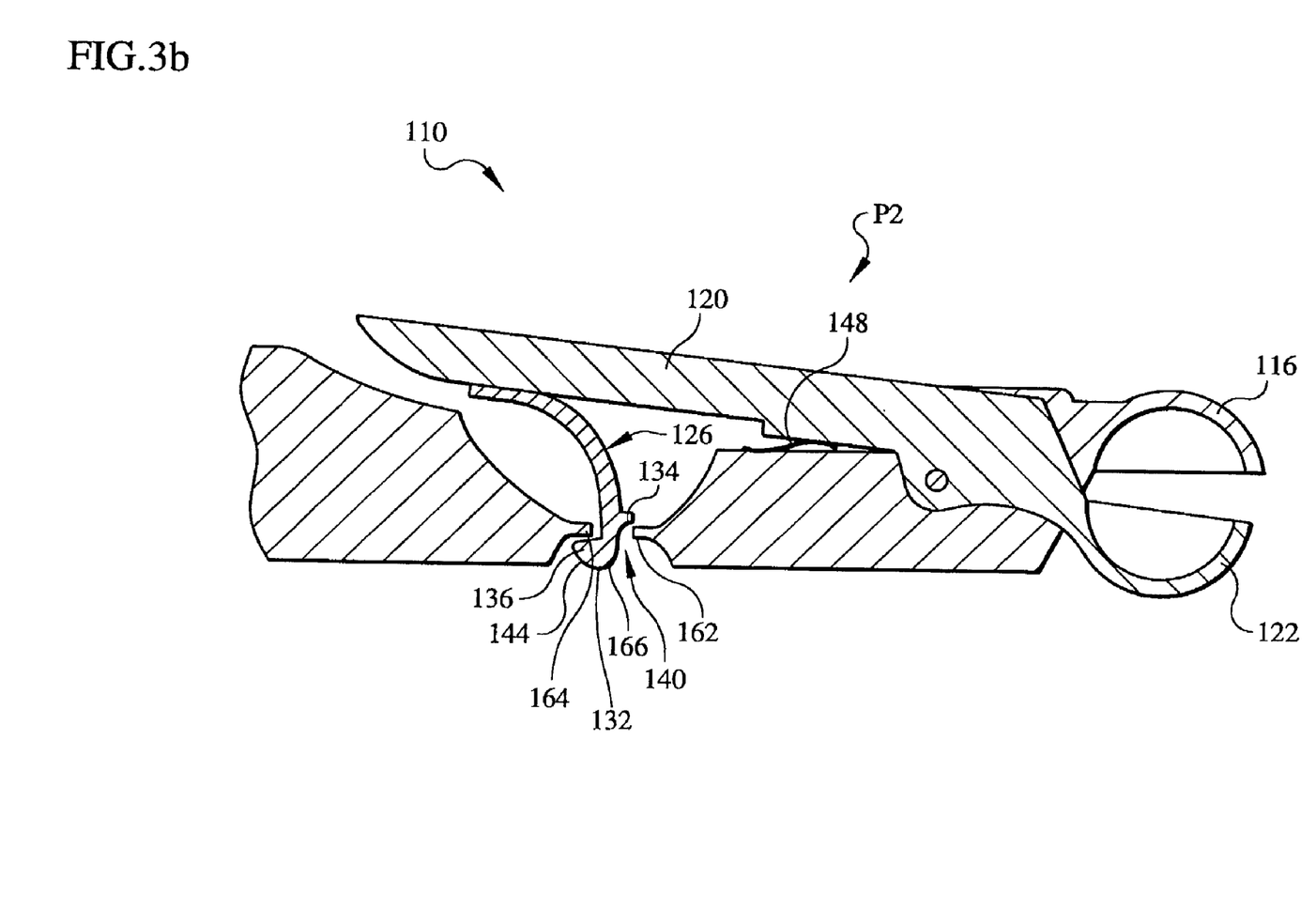

FIGS. 3a and 3b show another alternative embodiment of an instrument 110 of the present invention having a bi-directional double-catch latch 126. Latch 126 is somewhat similar to double-catch latch 26 of FIGS. 1a–1c, but instead of latch 126 having first and second catches 34, 36 located on the same side of the latch as one another, first catch 134 may be located on the side of the latch opposite the side containing second catch 136. This arrangement can provide dental instrument 10 with a safety feature that prevents a user from inadvertently opening lever arm 120 from its closed position P1 (FIG. 3a) directly to an open position (not shown, but similar to open position P3 of FIG. 1c) when the user intends to engage the lever arm into intermediate position P2 (FIG. 3b). Although the dual catches 34, 36 used in the embodiment of FIGS. 1a–1c reduce the possibility of inadvertently opening jaws 16, 22 in that both catches must be cleared before the jaws are sufficiently opened to permit a tool 12 to drop out, some users of the dental instrument of the present invention may find preferable the safety design featuring opposing catches 134, 136. In any event, inadvertent opening of jaws 16, 22 may cause tool 12 engaged with the jaws to become disengaged therefrom and drop into a patient's mouth or fall onto a floor or other surface below instrument 10.

Describing in more detail the safety feature provided by latch 126 of FIGS. 3a and 3b, the latter can prevent this inadvertent opening by requiring a user to move the latch in a first direction, e.g., away from jaws 116, 122, when moving lever arm 120 from closed position P1 to intermediate position P2 and in a second direction opposite the first direction, e.g., toward the jaws, when moving the lever arm between intermediate position P2 and an open position. Accordingly, rim 142 of aperture 140 may include an anterior stop 162 for engaging first catch 134 and a posterior stop 164 for engaging second catch 136 when lever arm 120 is in closed position P1 and intermediate position P2, respectively. To move lever arm 120 from closed position P1 to intermediate position P2, a user may engage a finger with surface 166 of second end 132 of latch 126 and move the latch in a direction generally away from jaws 116, 122, causing first catch 134 to disengage anterior stop 162 of rim 142 and also generally causing second catch 136 to engage posterior stop 164 of the rim as biasing spring 148 (FIG. 3b) biases lever arm 120 into intermediate position P2. If the user desires to move lever arm 120 to an open position (not shown) from intermediate position P2, the user may engage a finger with surface 144 and move latch 126 in a direction generally toward jaws 116, 122, causing second catch 136 to disengage posterior stop 164 of rim 142, allowing user to move the lever arm into an open position.

Figure 4A:
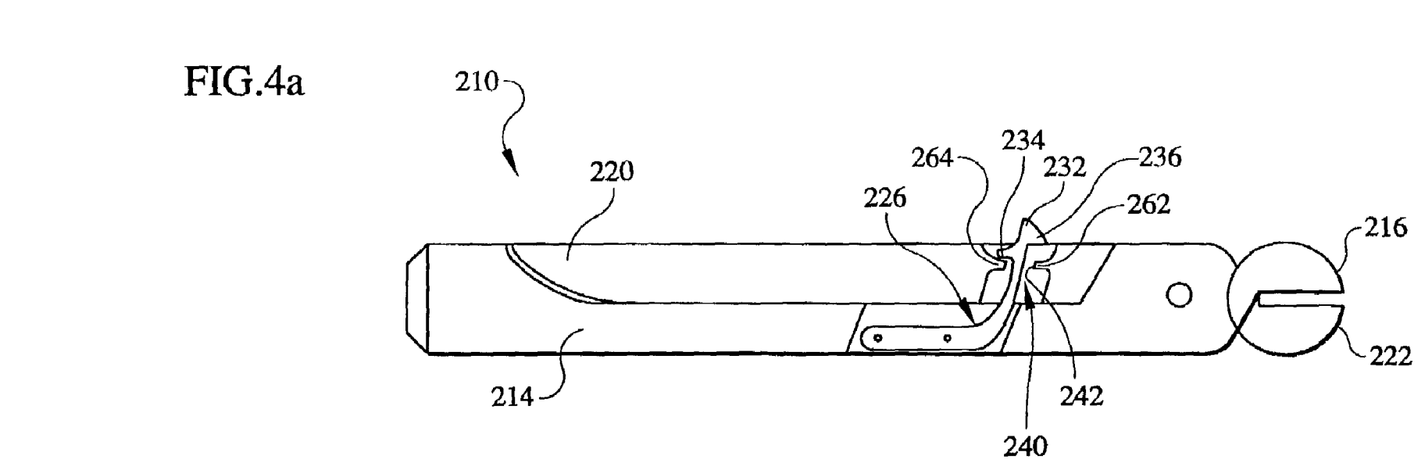
FIGS. 4a and 4b are, respectively, a side elevational view and a plan view of another alternative dental instrument of the present invention having a side-mounted bi-directional double-catch latch.
Figure 4B:
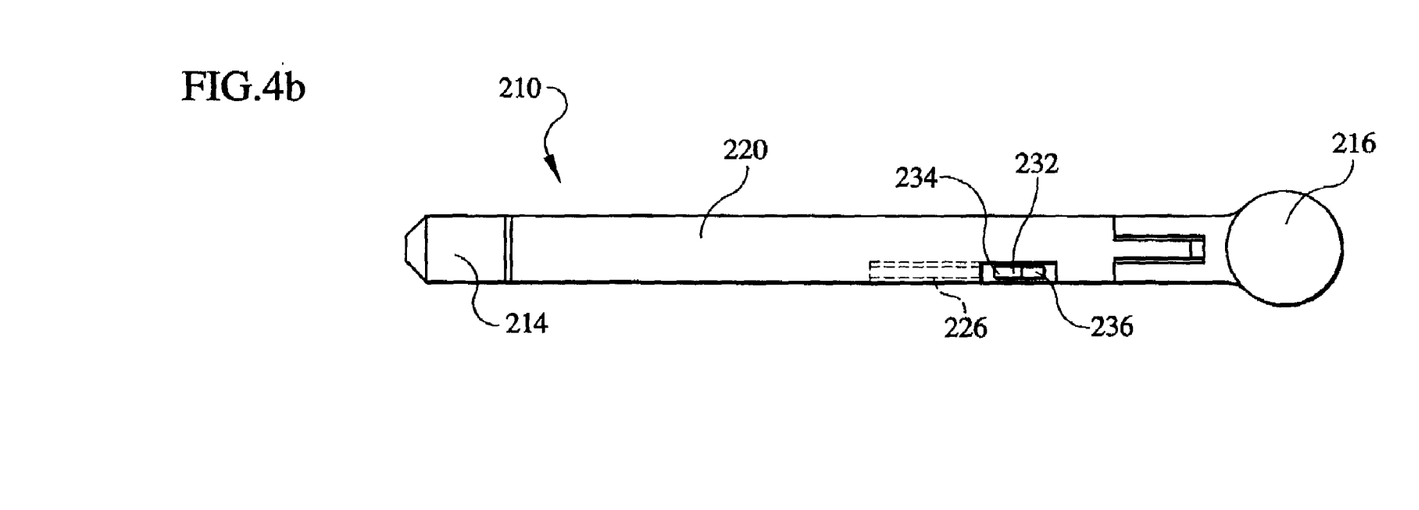

FIGS. 4a and 4b show yet another embodiment of an instrument 210 of the present invention, having a side-mounted latch 226, rather than the centrally-mounted latches 26, 126 of FIGS. 1 and 3. Side-mounted latch 226 may be similar to the bi-directional double-catch latch 126 of FIGS. 3a and 3b, i.e., have first and second catches 234, 236 that engage, respectively, corresponding posterior and anterior stops 264, 262 of rim 242 of aperture 240 and allow a user to release lever arm 220 from a closed position (shown) to an intermediate position (not shown, but similar to intermediate position P2 shown in FIG. 1b) by moving second end 232 of the latch toward jaws 216, 222, and release the lever arm from the intermediate position to an open position (not shown, but similar to open position P3 shown in FIG. 1c) by moving the second end of the latch away from the jaws.

Those skilled in the art will readily appreciate that although instrument 210 is shown having a bi-directional double-catch latch 226, instrument may have any one of the other latches described above or that otherwise fall within the scope of the present invention. Those skilled in the art will also appreciate that latch 226 may be attached to lever arm 220 rather than instrument body 214, as shown, and may be attached to either side of the lever arm at any location along instrument 210 desired. Of course, instrument 210 may be provided with jaws 216, 222 at both its ends in a manner similar to the instrument disclosed in U.S. Pat. No. 6,193,514.

A dental instrument of the present invention, e.g., any one of instruments 10, 110, 210, among others, has many advantages over prior art dental instruments. For example, a first advantage is that tool 12 can be rapidly replaced with another tool, or the orientation of tip 56 of the tool can be rapidly adjusted by snap-latching and snap-releasing the lever arm, e.g., lever arm 20. This allows dental procedures to be performed more quickly. Moreover, the latch, e.g., latch 26, allows tool 12 to be held in place with sufficient strength to prevent the tool from moving within the jaws, e.g., jaws 16, 22, and relative to the instrument body, e.g., instrument body 14, while performing dental procedures.

A second advantage is that instrument of the present invention, e.g., instrument 10, 110, 210, is designed so as to be readily cleansable. For example, the concave surfaces, e.g., concave surfaces 18, 24, and the aperture, e.g., aperture 40, can be cleaned with brushes, or other type scrubbing device. Moreover, the instrument can be readily cleaned when in the open position P3. The present instrument has a configuration similar to forceps, needle holders and the like, and so can be sterilized by scrubbing, ultrasonic cleansing, or autoclaving.

A third advantage is that the mechanisms for latching the lever arm, e.g., lever arm 40, and for clasping tool 12 are relatively simple. This not only makes it easy to clean and sterilize the instrument, as described above, but also makes the instrument affordable and easy to use.

Referring to FIG. 13, a fourth advantage is that the ability to quickly adjust and replace tool 12 can be achieved at both ends of the instrument, if jaws are provided at both ends of the instrument. This is advantageous when a given dental procedure involves, e.g., the use of different tools in repeated alternating order or a pair of tools having mirror image tool tips for performing the same step of the procedure at two different locations within a patients oral cavity, among other possibilities.

The preferred material for the elements comprising instrument 10, 110, 210 is stainless steel, though other materials, such as plastic, may be used as well.

While the present invention has been described in connection with preferred embodiments, it will be understood that it is not limited to those embodiments. In fact, it will be apparent that the present invention has applications other than that for a dental instrument, and will find utility in applications requiring snap-latching/snap-releasing and adjustment of a jaw-engaging end type apparatus requiring a high clasping strength. Accordingly, the present invention is intended to cover all alternatives, modifications and equivalents as may be included within the spirit and scope of the invention as defined in the appended claims.

What is claimed is:

1. An instrument, comprising:
   a body;
   a lever arm pivotably attached to said body and having three operative states consisting of a first detent state, a second detent state and a non-detent state;
   a latch having a first end attached to one of said body and said lever arm and a second end spaced from said first end and having a tip, said second end operatively configured so that said lever arm is selectably positionable only into ones of said three operative states by a user operating said latch; and
   first and second jaws wherein at least one of said first and second jaws is operatively coupled with said lever arm so that said at least one of said first and second jaws moves in conjunction with said lever arm when a user pivots said lever arm among said three operative states;
   wherein said latch has a longitudinal axis substantially perpendicular at least at said second end to said one of said body and said latch to which said latch is attached, said latch including a first catch located adjacent said tip of said latch and extending away from said longitudinal axis by a first distance and a second catch located between said first catch and said first end of said latch and extending away from said longitudinal axis by a second distance less than said first distance.

2. An instrument according to claim 1, further comprising a biasing member pivotably biasing said lever arm away from said body, said latch operatively configured so that after a user disengages said second catch from the one of said lever arm and body to which said latch is not attached with a finger and moves the finger out of contact with the latch, said biasing member causes said first catch to engage the one of said lever arm and body to which said latch is not attached so as to inhibit said lever arm from reaching said non-detent state.

3. An instrument according to claim 1, further including a stop attached to the other of said body and said lever arm, said second end of said latch including a finger-engaging surface for receiving a finger of a user to operate said latch, said first catch defining at least a portion of said finger-engaging surface.

4. An instrument according to claim 1, wherein said latch further includes a guide, a first side and a second side spaced from said first side, said guide operatively configured to guide said latch against one of said body and said lever arm during use so as to guide said latch into said second detent state from said first detent state and to inhibit said latch from moving from said first detent state to said non-detent state, said first side including said first and second catches and said second side including said guide.

5. An instrument according to claim 4, wherein said guide is located substantially opposite said second catch.

6. An instrument according to claim 1, wherein said latch includes a first side and a second side spaced from said first side, said first side including said first catch and a second side including said second catch.

7. An instrument according to claim 1, wherein said lever arm has a length and said body and said lever arm are each configured so that said lever arm conformally confronts said body along at least one-quarter of said length opposite said first and second jaws.

8. An instrument operable by a finger of a user, comprising:
a body having a first outer gripping surface;
a lever arm pivotably attached to said body and including a first end, a second end spaced from said first end and a second outer gripping surface located between said first end and said second end, said lover arm having a closed position in which said second end of said lever arm is proximate said body;
a depression formed in one of said first outer gripping surface and said second outer gripping surface;
a rim attached to one of said body and said lever arm and located in said depression, said rim defining at least a portion of an aperture;
a latch having a first end attached to the other of said body and said lever arm and a second end spaced from said first end, said latch comprising proximate said second end a first catch engagable with said rim so as to hold said lever arm in said closed position and said second end including a finger-engaging surface, said first catch being located within said depression and said finger engaging surface being located proximate said depression when said lever arm is in said closed position; and
first and second jaws wherein at least one of said first and second jaws is operatively coupled with said lever arm so that said at least one of said first and second jaws moves in conjunction with said lever arm when a user pivots said lever arm.

9. An instrument according to claim 8, wherein said latch further comprises a second catch defining at least a portion of said finger-engaging surface.

10. An instrument according to claim 9, wherein said latch has a longitudinal central axis, said second catch extends away from said longitudinal axis a first distance and said first catch extends away from said longitudinal central axis by a second distance greater than said first distance.

11. An instrument according to claim 8, wherein said lever arm bas exactly three operative states consisting of a first detent state, a second detent state and a non-detent state, said second end being operatively configured so that said lever arm is selectably positionable only into ones of said exactly three operative states.

12. An instrument according to claim 8, wherein said latch includes a first side and a second side spaced from said first side and said aperture is partially defined by a guide surface, said first side includes exactly two catches consisting of said first catch and a second catch.

13. An instrument according to claim 12, wherein said latch further including a protuberant guide located substantially opposite said second catch and engagable with said guide surface.

14. An instrument according to claim 8, wherein said body has a recess configured to receive at least said second end of said lever arm when said lever arm is in said closed position.

15. An instrument, comprising:
a body;
a lever arm pivotably attached to said body and including a first end, a second end spaced from said first end and a first outer gripping surface located between said first end and said second end, said lever arm having a closed position in which said second end of said lever arm is proximate said body;
said body having a second outer gripping surface that includes a recess for conformally receiving at least said second end of said lever arm when said lever arm is in said closed position so that portions of each of said first and second outer gripping surfaces proximate one another when said lever arm is in said closed position are substantially flush with one another;
a stop attached to one of said body and said lever arm and defining an aperture;
a latch attached to the other of said body and said lever arm, said latch including a first catch and a second catch each engagable with said stop; and
first and second jaws wherein at least one of said first and second jaws is operatively coupled with said lever arm so that said at least one of said first and second jaws moves in conjunction with said lever arm when a user pivots said lever arm.

16. An instrument according to claim 15, wherein, when said lever arm is in said closed position, at least said second end of said lever arm and said body define a substantially cylindrical handle.

17. An instrument according to claim 15, wherein said lever arm has exactly three operative states consisting of a first detent state, a second detent state and a non-detent state, and said second end of said latch is operatively configured so that said lever arm is selectably positionable only into ones of said exactly three operative states.

18. A system, comprising:
a dental tool having a bulbous jaw-engaging end and a working end; and
an instrument operatively configured to engage said dental tool, said instrument comprising:
a body;
a lever arm pivotably attached to said body and having three operative states consisting of a tool-gripping state in which said instrument grips said dental tool, a tool-adjusting state in which said instrument holds said dental tool so that said working end of said dental tool can be moved relative to said instrument and a tool-release state in which said dental tool may be disengaged from said instrument;
a latch attached to one of said body and said lever arm, said latch operatively configured so that said lever arm is selectably positionable only into ones of said three operative states; and first and second jaws, wherein at least one of said first and second jaws is operatively coupled with said lever arm so that said at least one of said first and second jaws moves in conjunction with said lever arm when a user pivots said lever arm, said first and second jaws defining a cavity that conformally confronts said bulbous jaw-engaging end of said dental tool when said lever arm is in each of said tool-gripping state and said tool-adjusting state.

19. A system according to claim 18, wherein said dental tool includes a substantially spherical jaw-engaging end and each of said first and second jaws defines a substantially hemispherical cavity for conformally engaging said substantially spherical jaw-engaging end.

20. A system according to claim 18, wherein said instrument further includes a stop attached to the other of said body and lever arm, said second end of said latch includes a finger-engaging surface for receiving a finger of a user for the user to disengage one of said first catch and said second catch from said stop when that one of said first catch and second catch is engaged with said stop, said first catch defining at least a portion of said finger-engaging surface.

21. A method of engaging a dental tool with an instrument comprising a lever arm, a first jaw, a second jaw movable with the lever arm and relative to the first jaw, a first stop, a latch that includes a first catch and a second catch spaced from the first catch, and a movable end having a finger-engaging surface for moving the lever arm from a first position to a second position, comprising in the following order the steps of:
  engaging a finger with the finger-engaging surface;
  disengaging the first catch from the stop by moving the movable end of the latch in a first direction with said finger;
  pivoting the lever arm a first amount to open the jaws a corresponding amount;
  engaging the second catch with the stop;
  disengaging the second catch from the stop;
  engaging a dental tool with said first and second jaws; and
  engaging said first catch with said stop.

22. A method according to claim 21, wherein the instrument further comprises a guide surface and the latch further includes a protuberant guide, the method further including, following the step of disengaging the first catch from the stop, engaging the protuberant guide with the guide surface.

23. A method according to claim 21, further comprising, following the step of pivoting the lever arm a first amount, the step of disengaging the second catch of the latch from the stop by moving the movable end of the latch in a second direction opposite the first direction to pivot the lever arm a second amount to further open the jaws.

* * * * *